United States Patent
Terrill

(10) Patent No.: US 11,666,449 B2
(45) Date of Patent: Jun. 6, 2023

(54) KEELED GLENOID IMPLANT

(71) Applicant: Howmedica Osteonics Corp., Mahwah, NJ (US)

(72) Inventor: Lance N. Terrill, League City, TX (US)

(73) Assignee: Howmedica Osteonics Corp., Mahwah, NJ (US)

( * ) Notice: Subject to any disclaimer, the term of this patent is extended or adjusted under 35 U.S.C. 154(b) by 73 days.

(21) Appl. No.: 16/936,804

(22) Filed: Jul. 23, 2020

(65) Prior Publication Data
US 2021/0030552 A1 Feb. 4, 2021

Related U.S. Application Data

(60) Provisional application No. 62/880,147, filed on Jul. 30, 2019.

(51) Int. Cl.
*A61F 2/40* (2006.01)
*A61F 2/30* (2006.01)

(52) U.S. Cl.
CPC .. *A61F 2/4081* (2013.01); *A61F 2002/30433* (2013.01); *A61F 2002/30878* (2013.01);
(Continued)

(58) Field of Classification Search
CPC .......... A61F 2/4081; A61F 2002/30433; A61F 2002/30878; A61F 2002/4085; A61F 2310/00011; A61F 2/30767; A61F 2002/30011; A61F 2002/30158; A61F 2002/305; A61F 2002/30578; A61F 2002/30616; A61F 2002/30736;
(Continued)

(56) References Cited

U.S. PATENT DOCUMENTS 4,964,865 A 10/1990 Burkhead et al.
5,702,447 A 12/1997 Walch et al.
(Continued)

FOREIGN PATENT DOCUMENTS

EP 1639967 A1 3/2006
EP 2446859 B1 4/2014

OTHER PUBLICATIONS

Extended European Search Report including Written Opinion for Application No. EP20188284.2, dated Feb. 3, 2021, pp. 1-7.

*Primary Examiner* — Brian A Dukert
(74) *Attorney, Agent, or Firm* — Lerner David LLP

(57) ABSTRACT

A prosthetic glenoid implant may include a polymer bearing component, a metal base component, and a plurality of fixation members. The bearing component may have a first surface adapted to articulate with a humeral head, and an opposing second surface including a first mating feature. The base component may have a first surface and a bone-contacting surface, the first surface having a second mating feature adapted to engage the first mating feature, the bone-contacting surface adapted to contact the native glenoid. The base component may define a plurality of apertures. The fixation members may each have a head and a threaded shaft adapted to pass through a corresponding one of the plurality of apertures, the head of each fixation member adapted to be positioned within a recess defined between the base component and the bearing component in an assembled condition of the prosthetic glenoid implant.

15 Claims, 14 Drawing Sheets

(52) U.S. Cl.
CPC ............... *A61F 2002/4085* (2013.01); *A61F 2310/00011* (2013.01)

(58) Field of Classification Search
CPC .... A61F 2002/30784; A61F 2002/3092; A61F 2002/3093; A61F 2002/30884; A61F 2002/30889; A61F 2002/30891; A61F 2002/30897; A61F 2/40; A61B 17/1666; A61B 17/1604
See application file for complete search history.

(56) References Cited

U.S. PATENT DOCUMENTS

| | | | |
|---|---|---|---|
| 6,070,820 A | 6/2000 | Young et al. | |
| 6,379,386 B1 | 4/2002 | Resch et al. | |
| 6,589,281 B2 | 7/2003 | Hyde, Jr. | |
| 6,679,916 B1 | 1/2004 | Frankie et al. | |
| 7,879,275 B2 | 2/2011 | Smith et al. | |
| 8,920,508 B2 | 12/2014 | Iannotti et al. | |
| 10,188,408 B2 | 1/2019 | Rouyer et al. | |
| 10,722,374 B2 * | 7/2020 | Hodorek | A61F 2/4081 |
| 2007/0142917 A1 * | 6/2007 | Roche | A61F 2/4081 623/19.11 |
| 2011/0153023 A1 * | 6/2011 | Deffenbaugh | A61F 2/4081 623/19.11 |
| 2017/0189092 A1 | 7/2017 | Bonutti et al. | |
| 2021/0137703 A1 * | 5/2021 | Roche | A61B 5/0031 |

* cited by examiner

KEELED GLENOID IMPLANT

CROSS-REFERENCE TO RELATED APPLICATIONS

This application claims priority to the filing date of U.S. Provisional Patent Application No. 62/880,147, filed Jul. 30, 2019, the disclosure of which is hereby incorporated by reference herein.

BACKGROUND OF THE DISCLOSURE

Over time and through repeated use, bones and joints can become damaged or worn. For example, repetitive strain on bones and joints (e.g., through athletic activity), traumatic events, and certain diseases (e.g., arthritis) can cause cartilage in joint areas, for example, which normally provides a cushioning effect, to wear down. When the cartilage wears down, fluid can accumulate in the joint areas, resulting in pain, stiffness, and decreased mobility. The same can happen in cases where tendons in a joint become lax or soft tissues in or adjacent the joint become damaged or worn.

Arthroplasty procedures can be used to repair such damaged joints. During a typical arthroplasty procedure, an arthritic or otherwise dysfunctional joint can be remodeled or realigned. A prosthesis or prostheses can be implanted to repair the damaged region(s). Arthroplasty procedures may take place in any of a number of different regions of the body, such as the knees, hips, shoulders, or elbows, for example. One type of arthroplasty procedure is a shoulder arthroplasty, in which a damaged shoulder joint may be replaced with prosthetic implants. The shoulder joint may have been damaged by, for example, arthritis (e.g., severe osteoarthritis or degenerative arthritis), trauma, or a rare destructive joint disease.

Prostheses that are implanted into a damaged region may provide support and structure to the damaged region, and may help to restore the damaged region, thereby enhancing its functionality. Prior to implantation of a prosthesis in a damaged region, the damaged region may be prepared to receive the prosthesis. In the case of a shoulder arthroplasty procedure, one or more of the bones in the shoulder area, such as the humerus and/or glenoid, may be treated (e.g., cut, drilled, reamed, and/or resurfaced) to provide one or more surfaces that can align with the implant and thereby accommodate the implant.

In a typical shoulder arthroplasty procedure, the native humeral head is replaced with a prosthetic humeral head, and a native glenoid is replaced with a prosthetic glenoid, with the prosthetic humeral head configured to articulate with respect to the prosthetic glenoid. However, it should be understood that, in some procedures, only one prosthetic component may be implanted into the joint, with the remaining native humeral head (or glenoid) configured to articulate with respect to the implant.

When implanting a prosthetic glenoid, as is typical with prosthetic joint implants, it is important that the implant is securely fixed to the anatomy. In order to securely fix a prosthetic glenoid component to the glenoid vault, one possible solution is to include fixation structures that extend deep into the glenoid vault for enhanced fixation. However, this may be difficult to accomplish because there is a wide variety of shapes of glenoid vaults among the population. Further, implanting fixation components deep into the glenoid vault may be problematic from the standpoint of revision procedures. In other words, if a second glenoid implant must be implanted during a second joint replacement procedure after the first joint replacement procedure, the first glenoid implant needs to be removed prior to implanting the second glenoid implant. If the first glenoid implant has fixation structures extending deep into the glenoid vault, a significant amount of native bone may need to be removed while in order to remove the first glenoid implant, which may make it difficult to effectively secure the second glenoid implant into the native anatomy.

BRIEF SUMMARY

According to one aspect of the disclosure, a prosthetic glenoid implant is for replacing a native glenoid. A bearing component has a first articulating surface adapted to articulate with a native or prosthetic humeral head, and a second surface opposite the first surface, the bearing component being formed of a polymer, the second surface including a first mating feature. A base component has a first surface and a bone-contacting surface, the first surface of the base component having a second mating feature adapted to engage the first mating feature in an assembled condition of the prosthetic glenoid implant, the bone-contacting surface adapted to contact the native glenoid, the base component being formed of metal and defining a plurality of apertures extending from the first surface of the base component to the bone-contacting surface of the base component. A plurality of fixation members each have a head and a threaded shaft, the threaded shaft of each fixation member adapted to pass through a corresponding one of the plurality of apertures, the head of each fixation member adapted to be positioned within a recess defined between the base component and the bearing component in an assembled condition of the prosthetic glenoid implant.

The bone-contacting surface of the base component may include an augment portion extending away from the bearing component in the assembled condition of the prosthetic glenoid implant, the augment portion having a convexity adapted to contact a concave neoglenoid portion of the native glenoid. At least one of the plurality of apertures may be positioned within the augment component.

The plurality of apertures may include a first group of peripheral apertures positioned adjacent an outer perimeter of the base component, and a central aperture substantially centered with respect to the outer perimeter of the base component. The central aperture may be positioned within a collet member extending away from the bone-contacting surface of the base component, the collet member adapted to expand upon receiving a collet screw therein.

The first mating feature may be a peripheral recess and the second mating feature may be a peripheral rim adapted to be received within the peripheral recess. Alternately, the first mating feature may be a peripheral rim and the second mating feature may be a peripheral recess, the peripheral rim being adapted to be received within the peripheral recess.

The base component may include a keel extending away from the bone-contacting surface, the keel being generally trapezoidal. The keel may have a length in a length direction extending away from the bone-contacting surface, and a width in a direction transverse the length direction, the width being smaller than the length. The keel may include a window defining a recess. The recess may be generally trapezoidal. The recess may include an array of circular openings. The base component may include a first slot extending from the first surface of the base component to the bone-contacting surface of the base component, the first slot being positioned adjacent the keel on a first side of the keel. The base component may include a second slot extending from the first surface of the base component to the bone-contacting surface of the base component, the second slot being positioned adjacent the keel on a second side of the keel opposite the first side of the keel.

The second surface of the bearing component may include a substantially circular extension member, the extension member having a plurality of recesses interrupting the circular extension member to define a plurality of individual extension members. Each of the individual extension members may include an anti-rotation protrusion extending in a direction radially away from a center of the circular extension member. The first surface of the base component may include a substantially circular member interrupted by a plurality of notches, each anti-rotation protrusion adapted to be received within a corresponding one of the plurality of notches in an assembled condition of the prosthetic glenoid implant.

DETAILED DESCRIPTION

As used herein, the term "proximal" means closer to the patient's heart, and the term "distal" means farther away from the patient's heart, when used in reference to a glenoid implant, when the glenoid implant is implanted in an intended orientation. Similarly, the term "anterior" means closer to the front of the patient, while the term "posterior" means closer to the rear of the patient. The term "superior" means closer to the patient's head, while the term "inferior" means closer to the patient's feet. The term "medial" means closer to the mid-line of the patient, while the term "lateral" means farther away from the mid-line of the patient. In the figures, like numbers refer to similar or identical parts. As used herein, the terms "substantially," "generally," "approximately," and "about" are intended to mean that slight deviations from absolute, for example plus or minus 10%, are included within the scope of the term so modified. When ranges of values are described herein, those ranges are intended to include sub-ranges. For example, a recited range of 1 to 10 includes 2, 5, 7, and other single values, as well as all sub ranges within the range, such as 2 to 6, 3 to 9, 4 to 5, and others.

Figure 1:
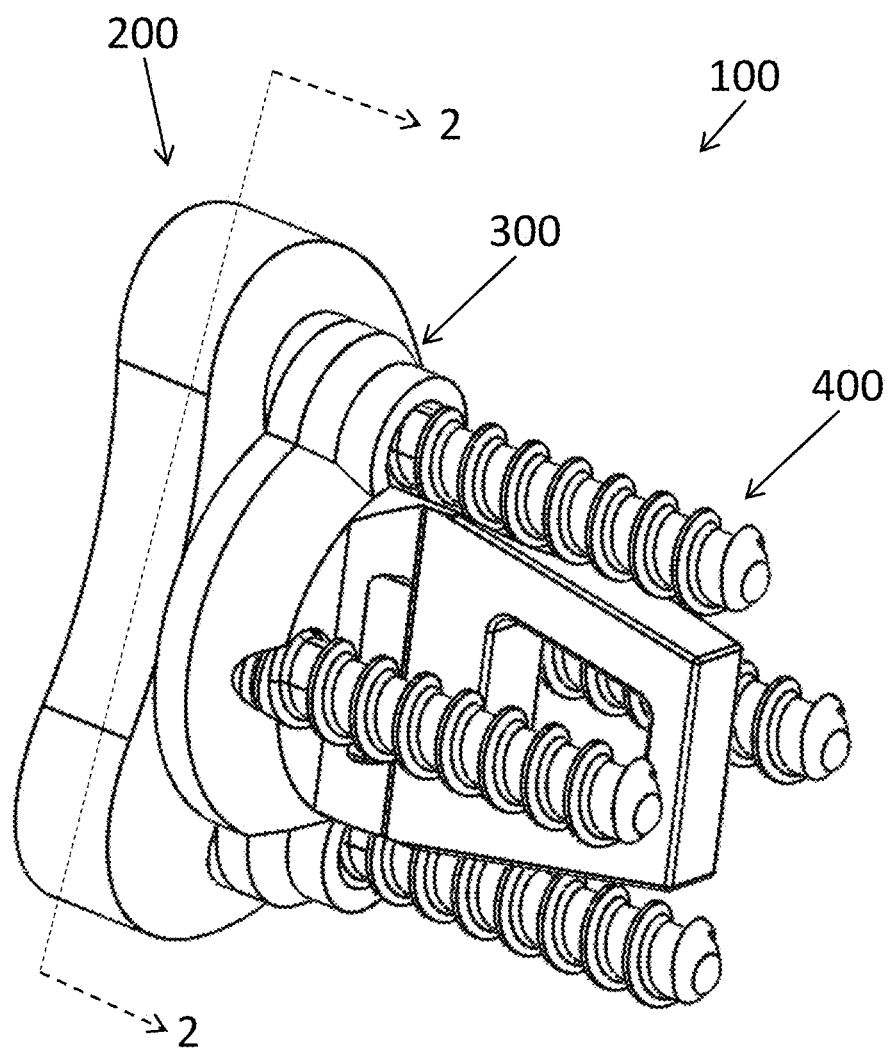
FIG. 1 is a perspective view of a prosthetic glenoid implant according to an aspect of the disclosure.
Figure 2:
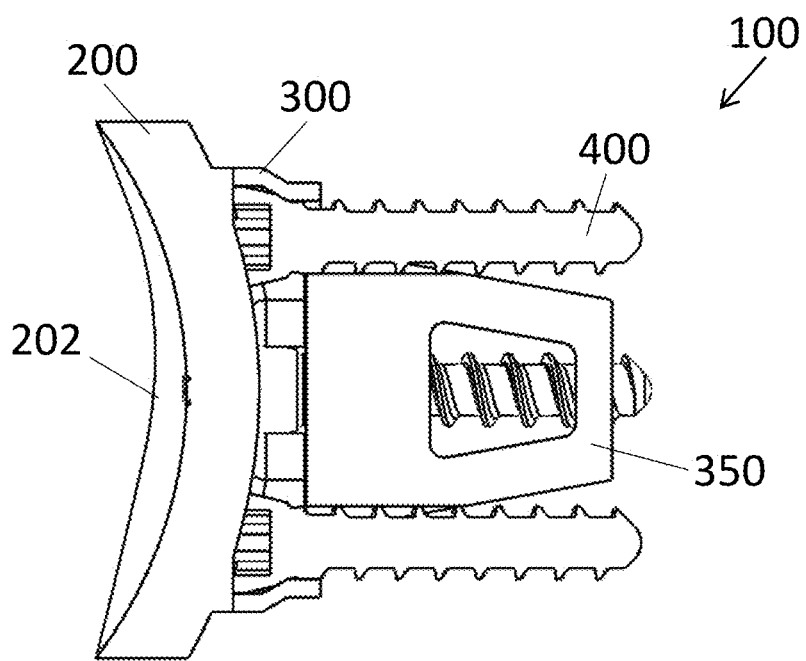
FIG. 2 is a cross-section of the glenoid implant of FIG. 1 taking along the section line 2-2 of FIG. 1.

FIGS. 1-8 illustrate various views of a prosthetic glenoid implant 100 according to a first aspect of the disclosure. Referring to FIG. 1, implant 100 generally includes a bearing component 200, a base component 300, and one or more fixation components 400, although it should be understood that portions of base component 300 may also serve to provide an amount of fixation of the implant 100. FIG. 2 illustrates a section of implant 100 taken along the section line 2-2 of FIG. 1. Glenoid implant 100 may be symmetrical so that it is capable of being implanted on the glenoid of a left or right shoulder joint, although in some embodiments the implant 100 may be specific to the left or right shoulder joint.

Figure 3:
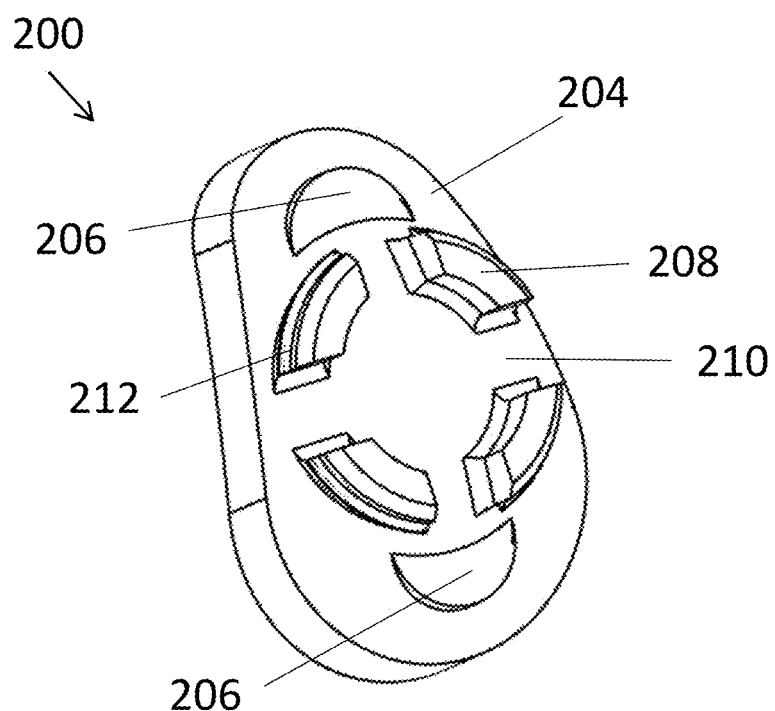
FIG. 3 is a perspective view of a medial surface of a bearing component of the glenoid implant of FIG. 1.

As best seen in FIGS. 2-3, bearing component 200 includes a lateral bearing surface 202 and a medial bone-contacting surface 202 opposite the bearing surface. Bearing component may be formed of any suitable biocompatible material, including a polymer, such as polyethylene, including ultra-high-molecular-weight polyethylene (UHMWPE). Bearing surface 202 may have a concave surface and a shape that generally matches the shape and concavity of a healthy glenoid. After implantation, the bearing surface 202 functions to allow a prosthetic or native humeral head to articulate against the bearing surface. In the view of FIG. 2, the top of bearing component 200 is the superior side, while the bottom of the bearing component is the inferior side.

Referring to FIG. 3, the bone-contacting surface 204 of bearing component 200 may include superior and inferior contact platforms 206. Superior and inferior contact platforms 206 may be generally semi-circular shaped and may present a substantially flat surface which corresponding surfaces of base 300 may contact in an assembled condition of the implant 100. In addition, the heads 410 of superior and inferior fixation members 400 may similarly contact the substantially flat surfaces of the superior and inferior contact platforms 206. It should be understood that the superior and inferior contact platforms 206 may be omitted, may have other shapes than shown, may be positioned other than shown, or may be provided in greater or fewer numbers than shown. The flat surfaces presented by the superior and inferior contact platforms 206 may be seen in FIG. 2, and the positioning, size, and number of the platforms complements the structure of the base 300 and/or the heads 410 of fixation members 400, described in greater detail below. Still further, the superior and inferior contact platforms 206 may assist in resisting rotation of bearing component 200 relative to base component 300.

Still referring to FIG. 3, a substantially circular rim 208 may extend from the bone-contacting surface 204 of bearing component 200. In the illustrated embodiment, rim 208 is formed by a plurality of individual protrusions that are separated from one another by recesses 210. As shown, rim 208 is formed of four semi-circular protrusions that are spaced about equally from one another, with each adjacent pair of semi-circular protrusions being separated by a void or recess 210. However, it should be understood that more or fewer recesses (including no recesses) may be provided instead, and rim 208 need not lie along a perfect circle, as other shapes may be suitable. In the illustrated embodiment, rim 208 is positioned between the superior and inferior contact platforms 206. In some embodiments, rim 208 may include mating features to assist in mating to base 300. For example, in the illustrated embodiment, the radially outward-facing surfaces of the protrusions forming the rim 208 may include either a recess or a rib 212 extending along the outer circumference for engaging a complementary recess or rib of the base 300, for example via a snap-fit, as will be explained in greater detail below.

Figure 4:
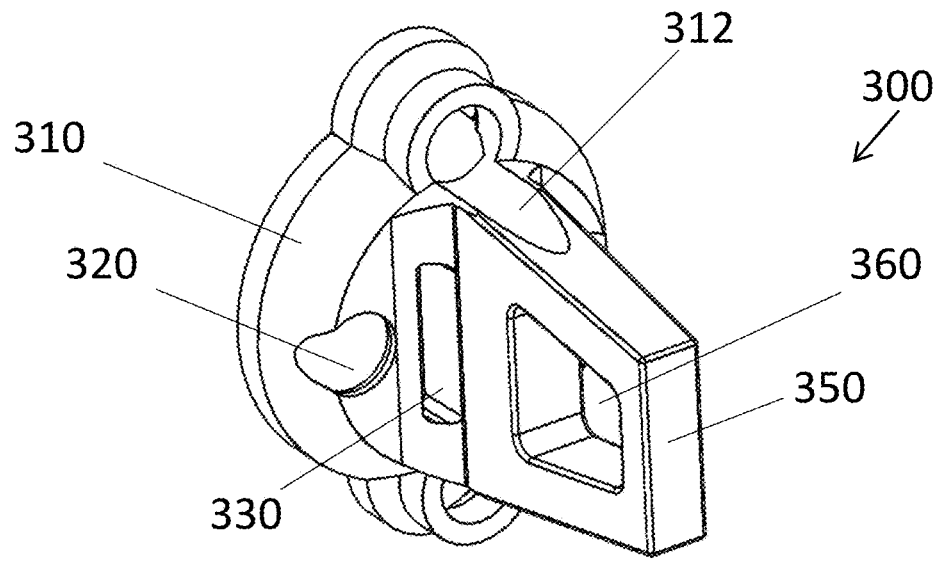
FIGS. 4-5 are various views of a base component of the glenoid implant of FIG. 1.
Figure 5:
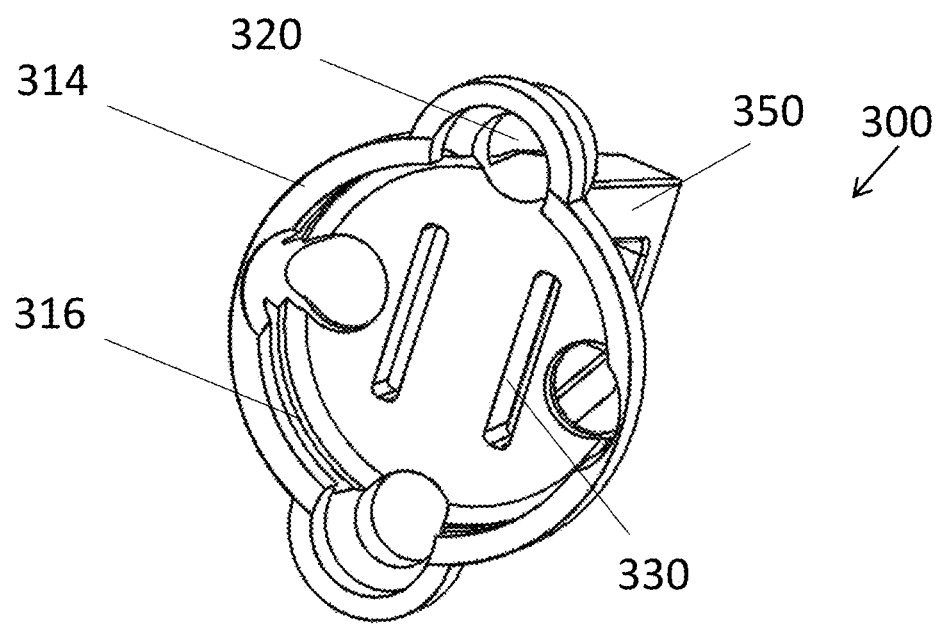
Figure 6:
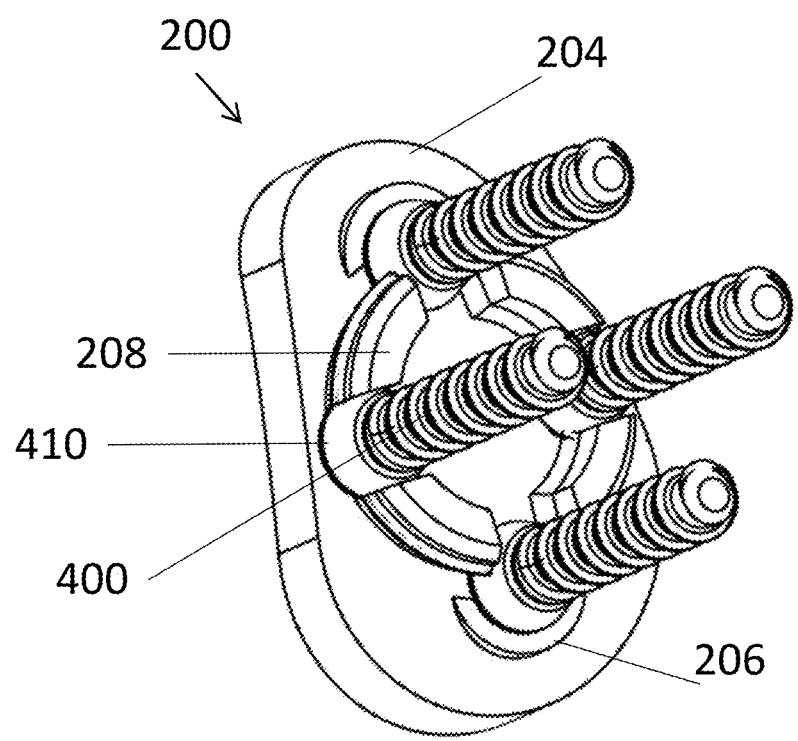
FIG. 6 is a perspective view of the implant of FIG. 1 with the base component omitted for purposes of illustration.
Figure 24:
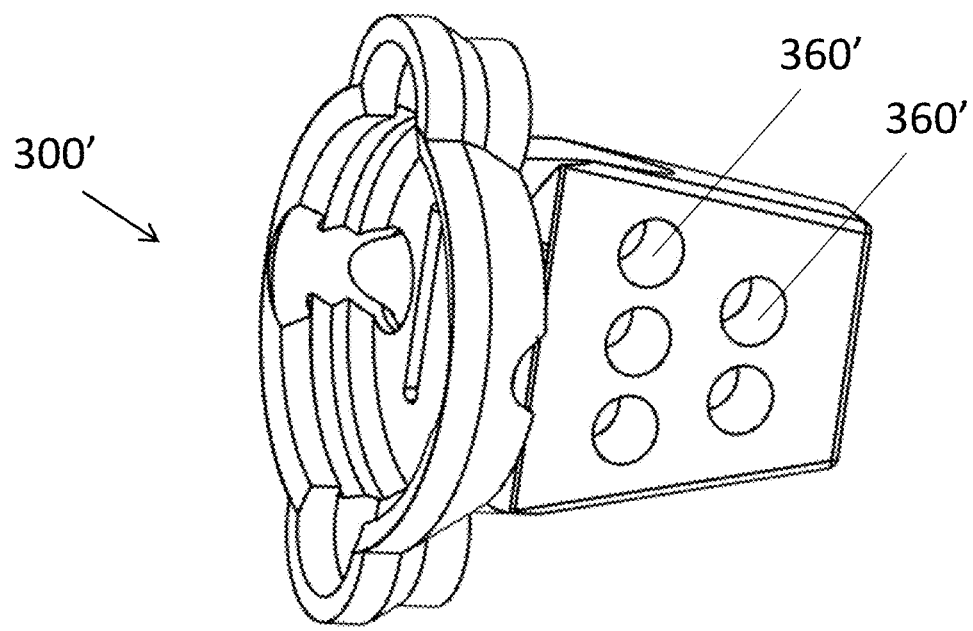
FIGS. 24-26 are perspective views of base components similar to that shown in FIG. 4, with alternative styles of openings in the keel.
Figure 25:
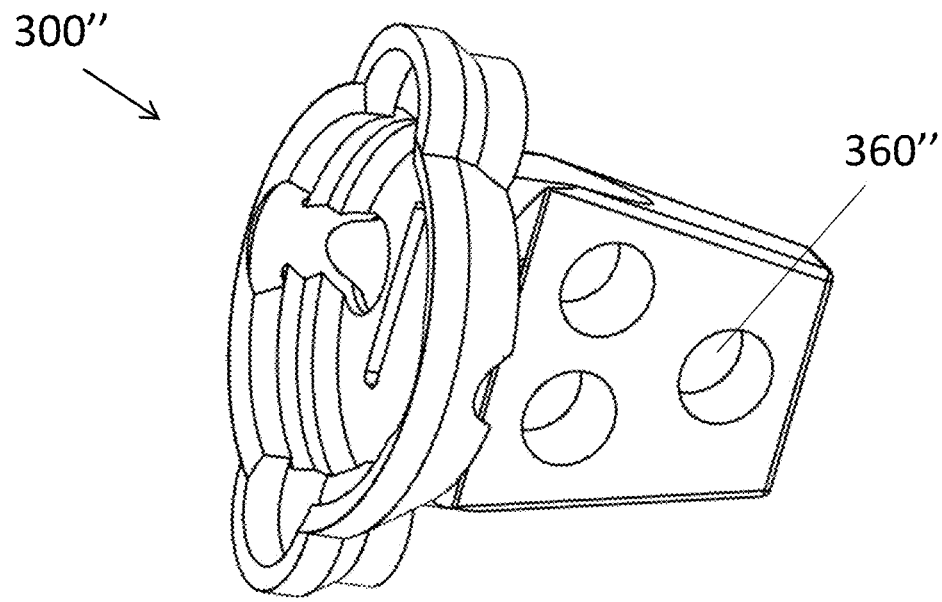
Figure 26:
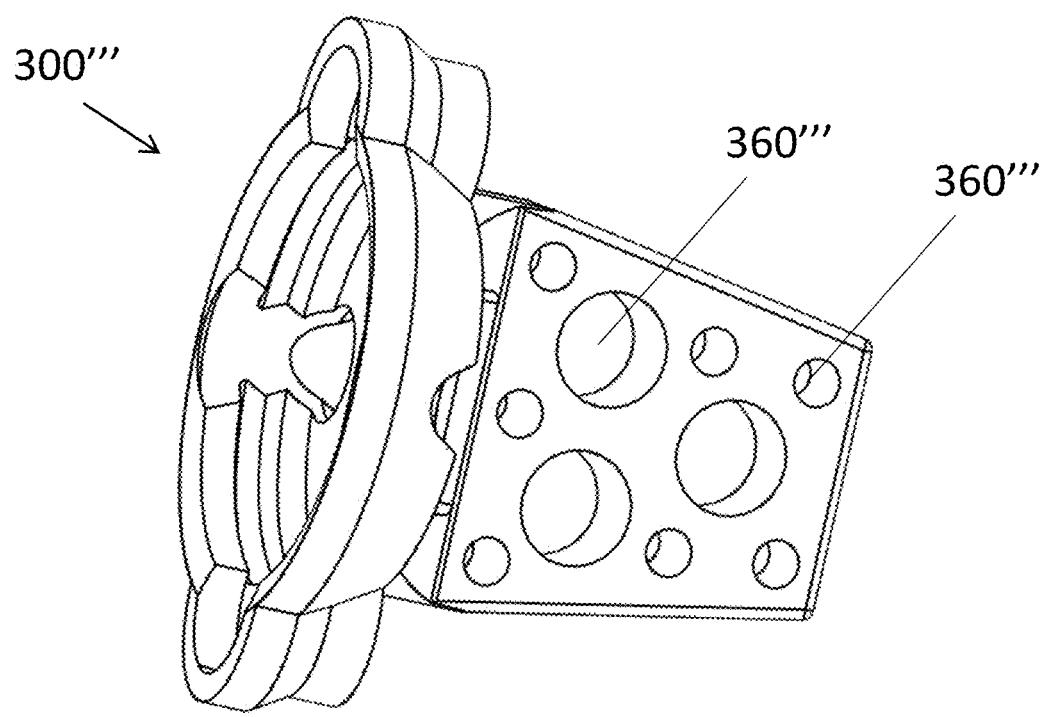

FIGS. 4-6 illustrate various views of base component 300. In some embodiments, base component 300 is formed as a unitary or monolithic structure. Base component 300 may be thought of as including two main portions, including a keel portion adapted extend into the glenoid vault to provide better fixation of the implant within the glenoid, and a base portion configured to connect the keel portion to the bearing component 200. Referring to FIGS. 2 and 4, keel 350 may extend medially from the remainder of the base component 300, so that in an assembled condition of the implant 100, the keel 350 extends away from the bone-contacting surface 204 of the bearing component 200. In the illustrated embodiment, keel 350 includes a relatively long lateral portion where it joins the remainder of the base component 300, a relatively short medial portion at the terminal end of the keel 350, and angled superior and inferior portions connecting the medial and lateral portions. In other words, in the illustrated embodiment, keel 350 is substantially trapezoidal. The keel 350 may have a length in a length direction extending away from bearing component 200, and a width in a direction transverse the length direction, the width being smaller than the length. Keel 350 may also include a recess, cut-out, or window 360 extending from the anterior surface of the keel 350 to the posterior surface of the keel 350. In the illustrated embodiment, the window 360 is also substantially trapezoidal, although other shapes may be suitable. In one example, instead of a trapezoidal window 360, keel 350 may include one or more circular through-holes, including for example, an array of circular through-holes. Examples of a circular array of through-holes are illustrated in FIGS. 24-26. FIG. 24 illustrates a base component 300' that is identical to base component 300, except that openings or windows 360' are provided as an array of five similarly sized circular through-holes arranged in a column of three openings 360' and a column of two openings 360' positioned medially to the three openings. FIG. 25 illustrates another example of a base 300" identical to base 300, except that base 300" includes three windows or openings 360" in the form of similarly sized circular through-holes arranged in a generally triangular pattern. FIG. 26 illustrates a further example of a base 300''' identical to base 300, except that base 300''' includes differently sized openings. In the example of FIG. 26, base 300''' includes three relatively large circular through-holes 360''' arranged in a generally triangular pattern similar to FIG. 25, but also includes a number of additional smaller circular through-holes 360''' positioned near the larger circular through-holes. It should be understood that FIGS. 24-26 are merely exemplary of possible positioning of arrays of circular through-holes in a keel similar to keel 350. The circular arrays of through-holes may allow bone ingrowth to be mechanically functional more quickly compared to a single larger individual window.

Keel 350 is shaped to extend relatively deeply into the glenoid vault, and the tapered superior and inferior surfaces of the keel may generally follow the contours of the native glenoid to allow for the keel to extend deep into the glenoid vault without compromising the outer cortical shell of the glenoid vault. The trapezoidal shape of keel 350 may also help resist rotation of the base component 300 after implantation, with the window 360 allowing for bone to enter the opening in the keel to further help stabilize the base component 300, while simultaneously reducing the weight and overall bulk of the base component 300. However, the weight and overall bulk of the base component 300 may not be a primary factor to take into consideration compared to the ability to achieve desired fixation. Preferably, base component 300 is formed of a biocompatible metal or metal alloy, such as titanium. Base component 300 may be provided with enhanced bone-ingrowth surfaces on all portions of the base component that are intended to contact bone, or otherwise at strategic locations only. For example, base component 300 may include a porous metal (such as porous titanium) surface to enhance bone growth into the base component 300 to enhance fixation over time. In one particular embodiment, the enhanced bone-ingrowth surfaces may be limited to the keel 350, for example to the anterior and posterior surfaces of the keel 350. This particular positioning may assist in a later revision procedure that utilizes cutting slots 330 in the base component 300, described in greater detail below.

Referring to FIGS. 4 and 5, base component 300 may include a generally circular base portion 310 including a plurality of apertures 320 for receiving portions of fixation members 400 therethrough. In the illustrated embodiment, the base portion 310 is partially circular, but includes superior and inferior extensions, which each include an aperture. These superior and inferior extensions may be configured to contact the superior and inferior contact platforms 206 of bearing component 200. The positioning of the superior and inferior extensions of base portion 310 may help provide space for the keel 350 to have the desired position and size. As best shown in FIG. 4, the base component 300 may include grooves 312 in the keel 350 where the superior and inferior extensions of the base portion 310 transition into the keel, with the grooves 312 contoured to provide clearance for superior and inferior fixation members 400 that extend through the superior and inferior apertures 320.

Referring to FIG. 5, the base portion 310 may include a substantially circular rim 314, although rim 314 may also include superior and inferior extensions. The circular portion of rim 314 may be configured to couple to the circular rim 208 of the bearing component 200, for example by a snap fit. To that end, rim 314 may include an interior lip or recess 316 for engaging with the rib 212 of rim 208. When the base component 300 is coupled to the bearing component 200, for example as shown in FIGS. 1 and 2, the superior and inferior apertures 320 of the base component 300 generally align with the superior and inferior voids or recesses 210 and/or the superior and inferior contact platforms 206 of bearing component 200. Similarly, the medial and lateral apertures 320 of the base component 300 generally align with corresponding medial and lateral voids or recesses 210. As a result, in the assembled condition of glenoid implant 100, the heads 410 of fixation members 400 are at least partially positioned in corresponding voids of recesses 210 of the bearing component 200, helping ensure that the bearing component 200 and the base component 300 cannot rotated with respect to one another. This is illustrated in FIG. 6, which shows the assembled glenoid implant 100 with base component 300 omitted from the view to illustrate the position of the heads 410 of the fixation components 400. It should be understood that, when the base component 300 is coupled to the bearing component 200, a space is defined between the base component and the bearing component in which the heads 410 of the fixation components 400 are at least partially located. However, it may be preferable to include anti-rotation features other than, or in addition to, the position of the heads 410, including for example the platforms 206 described above, or any of the anti-rotation features described elsewhere herein.

Referring back to FIGS. 4-5, base component 300 may include two cutting slots 330. In the illustrated embodiment, base component 300 includes two elongated slots 330 that are define openings adjacent the anterior and posterior surfaces of keel 350. The slots 330 may be used during a revision procedure to help cut bone. For example, a microtome, osteotome, or other cutting tool may be passed through the slots 330 during a revision procedure to cut the bone adjacent to the anterior and posterior portions of the keel 350. As noted above, the anterior and posterior portions of the keel may include enhanced bone-ingrowth surfaces so that the fixation between the anterior and posterior portions of the keel and the native bone becomes particularly strong. As is described in greater detail below, these features may allow for the benefit of keel 350 to deeply penetrate into the glenoid vault for secure fixation, while still allowing for a revision procedure that minimizes the amount of bone that must be cut away to explant the glenoid implant 100.

Figure 7:
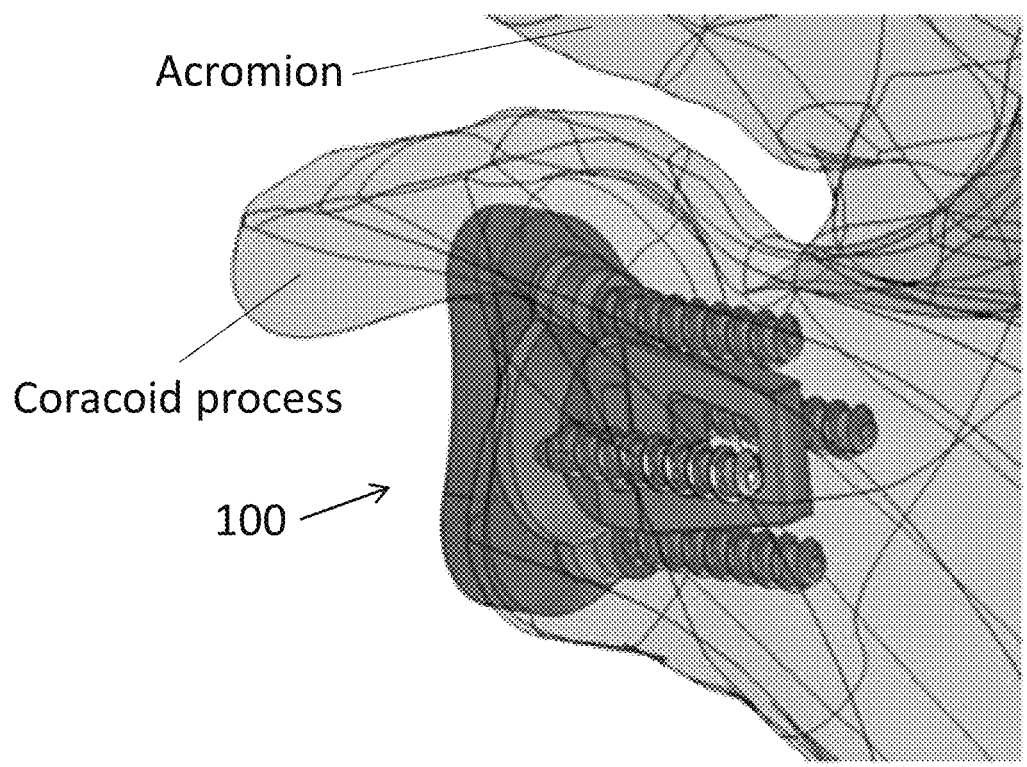
FIG. 7 is a highly schematic illustration of the glenoid implant of FIG. 1 implanted into a glenoid.

In an exemplary method of use, the patient's glenoid may be prepared, for example by reaming, prior to implantation of glenoid implant 100. Base component 300 may be implanted into the glenoid vault first. For example, a recess may be cut into the glenoid to receive the keel 350 in the desired orientation. Preferably, the recess is cut into the bone with a broach or a burr, with or without robotic assistance, although robotic assistance may be preferable. Although cement may be used to help fix the keel 350 into the glenoid, the fixation is preferably cementless. After advancing the base component 300 of, fixation members 400 may be inserted through the apertures 320 in the base component 300 and into the glenoid bone. In the illustrated embodiment, fixation members 400 are screws having a head 410 with a substantially flat proximal surface, and a threaded shaft for threading into the bone to further secure the base component 300 to the glenoid. Although various types of screws may be suitable for use as fixation members 400, in one example, the fixation members 400 are screws with a diameter of about 5.0 mm. After the fixation members 400 have been inserted to secure the base component 300 to the glenoid, the bearing component 200 may be coupled to the base component 300, for example via the snap-fit described above. The glenoid implant 100 may be configured as an "inlay" implant, as opposed to an "onlay" implant. As used herein, the term onlay refers to a baseplate or base component sitting on top of the prepared surface of the glenoid, whereas the term inlay refers to the baseplate or base component 300 being inset into the glenoid. In other words, according to one aspect of the disclosure, after being fully implanted, the base component 300 and fixation members may be positioned within the glenoid bone. FIG. 7 illustrates glenoid implant 100 in a final implanted position in the glenoid, with portions of the bone illustrated as transparent to show components of implant 100.

Figure 8:
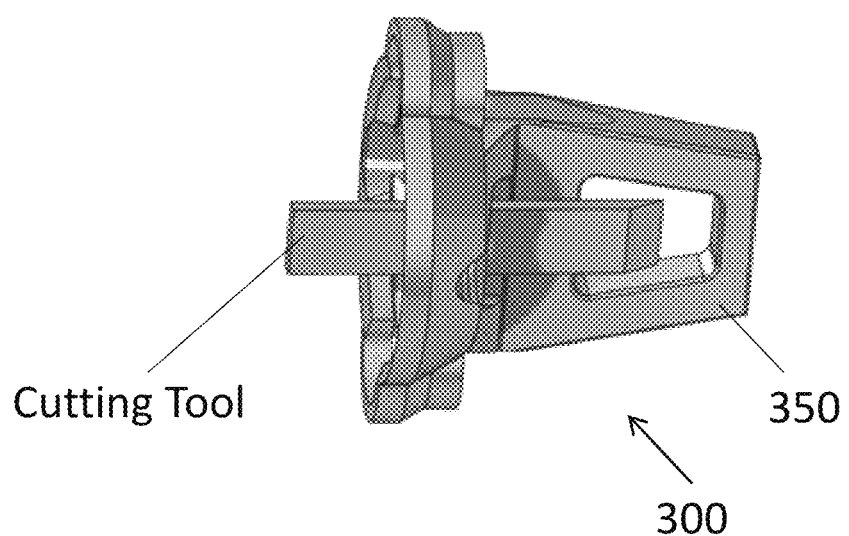
FIG. 8 is a schematic illustration of a cutting tool being used with the glenoid implant of FIG. 1.

If a revision procedure is desired, for example after glenoid implant 100 has been implanted for a length of time, the glenoid implant 100 may be explanted with a relatively small amount of bone needing to be removed given the amount of fixation structures provided on glenoid implant 100. For example, during a revision procedure, the shoulder joint may be accessed and the bearing component 200 may be disconnected from the base component 300, for example by pulling the bearing component to disengage the snap-fit (or other type) of connection between the two components. In other examples, a screw could be threaded into the bearing component 200 and the bearing component 200 could be levered out of the base component 300. Still in other embodiments, a removal tool may include a screw tip which can be threaded into the bearing component 200 while pushing against the base component 300 to provide relative motion between the bearing component 200 and the base component 300 to disconnect the two components. With the bearing component 200 removed, access to the heads 410 of the fixation members 400 is provided. The fixation members 400 may be removed from the bone, for example by unscrewing the screws. Finally, the base component 300 will need to be cut out from the glenoid vault, at least because of bone ingrowth that has occurred over time to fix the keel 350 to the bone in the glenoid. As shown in FIG. 8, a cutting tool such as a microtome or osteotome may be inserted through slots 330 to cut away bone adjacent the anterior and posterior surfaces of the keel 350. As noted above, these surfaces may include an enhanced bone-ingrowth surface, and the connection between the bone and the keel adjacent these surfaces may be particularly strong. With the bone adjacent the anterior and posterior surfaces of the keel 350 being cut away, the base component 300 may be removed from the glenoid vault, and the revision implant may be implanted according to the particular procedure for the revision implant.

As should be understood from the description provided above, glenoid implant 100 may provide various benefits, particularly including enhanced fixation while maintaining the ability to effectively perform a revision procedure. While keeled glenoid implants have been used in the past, they have not gained popularity because of the difficulty in performing revision procedures—a problem that the current disclosure mitigates. Further, many prior art glenoid implants have an onlay design in which a baseplate, which may be conceptually similar to the base components described herein, sits on the prepared glenoid surface, which may result in the joint being overstuffed with implant structure, compared to the present disclosure in which the base component may have an inlay design that reduces the amount of implant structure extending into the joint space. Since baseplate or base component inlay designs are sunk into the bone, they may have more stability than onlay designs to resist eccentric loading of the component. The present disclosure combines an inlaid baseplate or base component with a bearing component that covers the superior and inferior extremes of the glenoid surface. The reduced stiffness of the bearing component may improve load sharing in these regions of the glenoid as compared with traditional full-coverage baseplate or base component designs. As should be also be understood, an inlaid baseplate or base component design may also increase the available joint space relative to an onlay design, reducing the above-noted overstuffing.

FIGS. 9-13 illustrate components of a glenoid implant 1100 according to another embodiment of the disclosure. It should be understood that glenoid implant 1100 has many similar or identical features to glenoid implant 100, and thus only the differences are described in connection with glenoid implant 1100. In other words, unless noted otherwise, the components of glenoid implant 1100 are similar or the same as those described for glenoid implant 100, including possible variations described in connection with glenoid implant 100.

Figure 9:
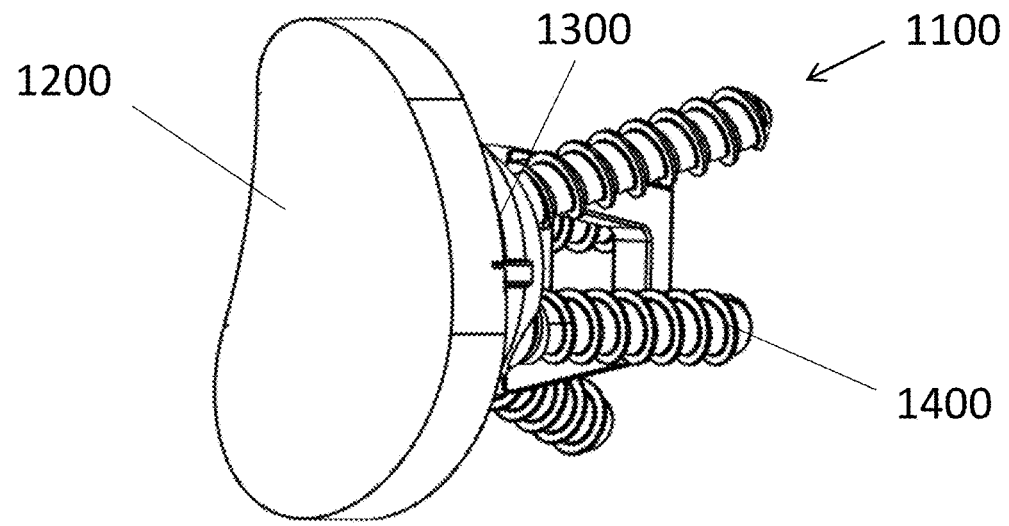
FIGS. 9-10 are perspective views of a prosthetic glenoid implant according to another aspect of the disclosure.
Figure 10:
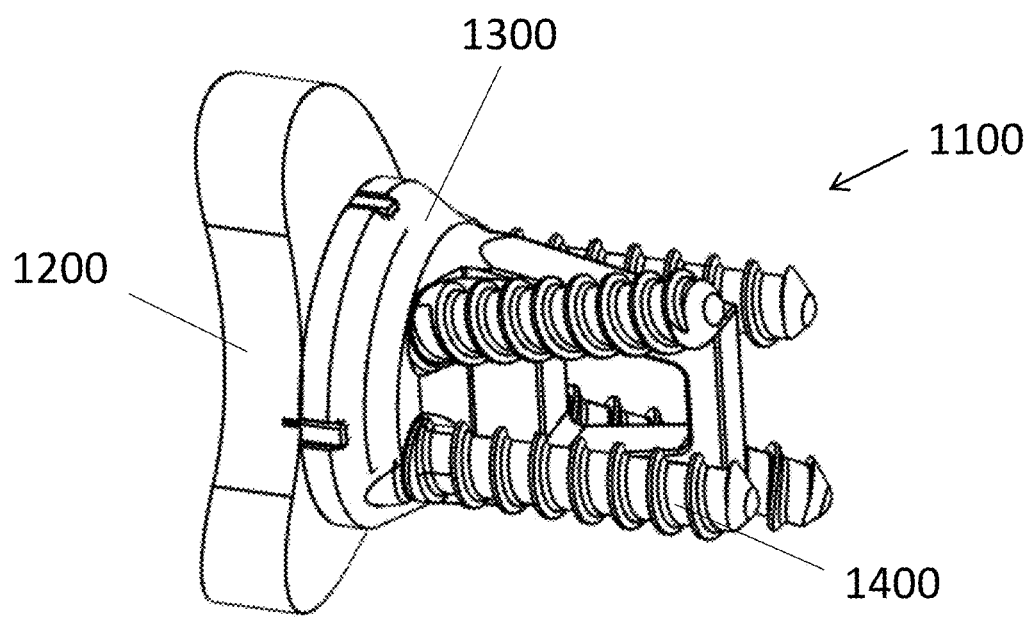
Figure 11:
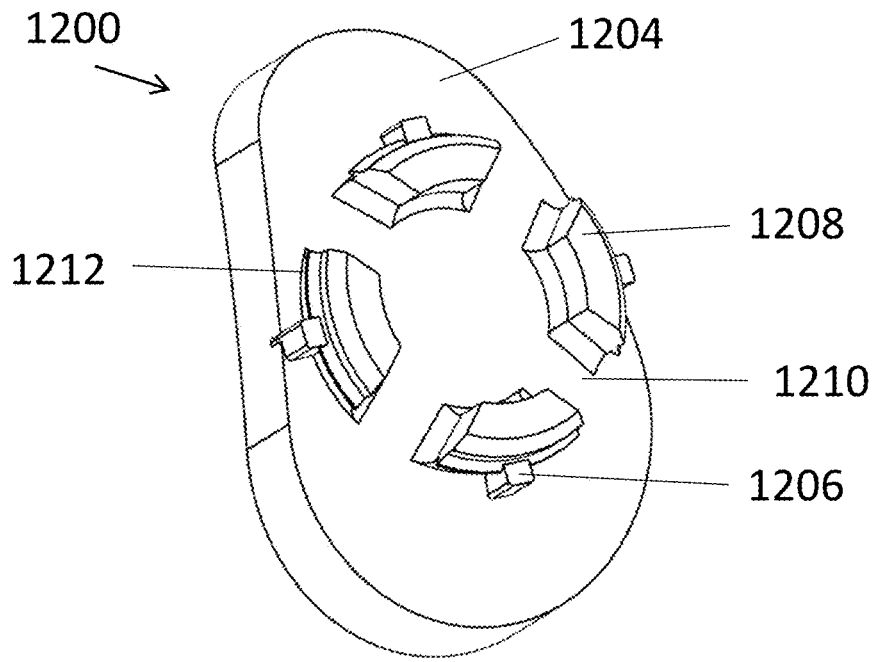
FIG. 11 is a perspective view of a bearing component of the glenoid implant of FIGS. 9-10.

FIGS. 9-10 are perspective views of glenoid implant 1100. Similar to glenoid implant 100, implant 1100 includes a bearing component 1200, a base component 1300, and fixation members 1400. A medial surface of bearing component 1200 is illustrated in FIG. 11. Similar to bearing component 200, bearing component 1200 includes a bone-contacting surface 1204, and a substantially circular rim 1208 extending from the bone-contacting surface. Rim 1208 is interrupted by recesses 1210, and may include a recess or rib 1212 for engaging with base component 1300. The main difference between bearing components 200 and 1200 is that bearing component 1200 includes tabs 1206 extending radially away from the center of rim 1208. As illustrated, each of the four portions of rim 1208 includes a tab 1206, although in some embodiments less than all of the portions of rim 1208 may include a corresponding tab 1206. As described below, tabs 1206 may assist in the engagement of bearing component 1200 to base component 1300, while simultaneously resisting the bearing component 1200 from rotating with respect to the base component 1300.

Figure 12:
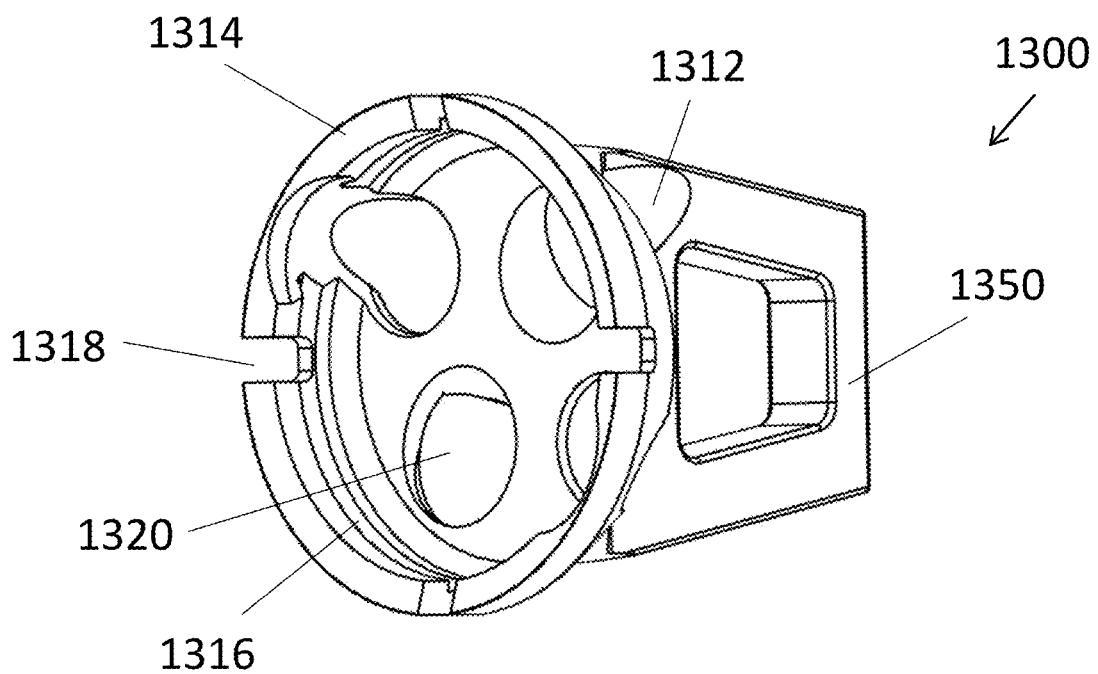
FIGS. 12-13 are perspective views of a base component of the glenoid implant of FIGS. 9-10.
Figure 13:
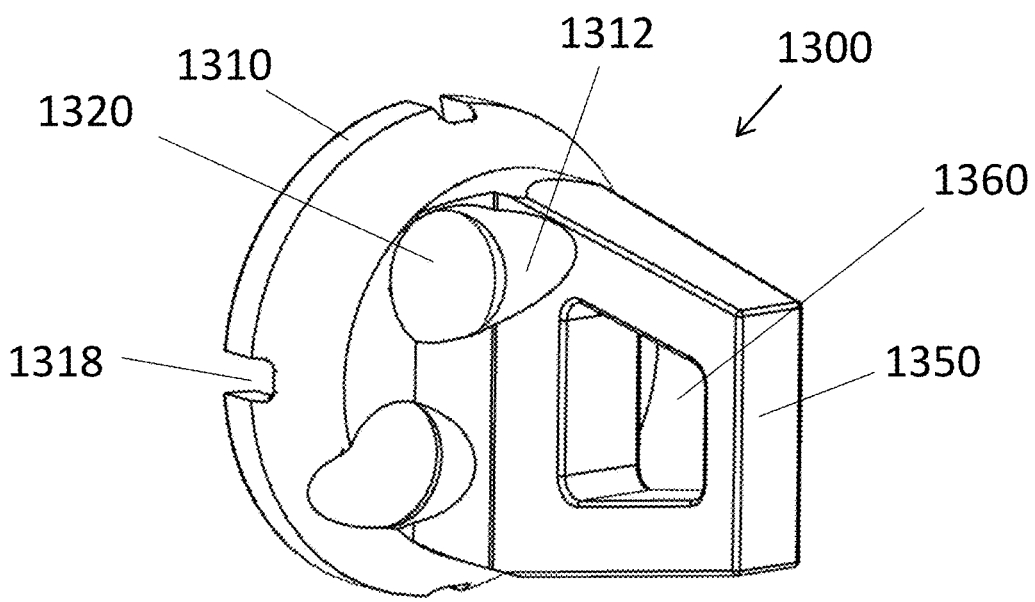

FIGS. 12-13 are perspective views of the base component 1300 of glenoid implant 1100. Base component 1300 may include a base portion 1310 and a keel 1350. Keel 1350, including the opening 1360 defined therein, may be substantially similar or identical to keel 350 and opening 360 of glenoid implant 100. Base portion 1310 may include a rim 1314 and an internal rib or recess 1316 to mate (for example via a snap-fit) with the recess or rib 1212 of bearing component 1200. Rim 1314 may be interrupted by a plurality of notches 1318 around the circumference of the rim 1314, the notches 1318 being sized, shaped, and positioned to receive a corresponding tab 1206 therein. In addition to the notches 1318, the main differences between base component 1300 compared to base component 300 are that base component 1300 does not include slots, and does not include superior and inferior extensions similar to base component 300. As with base component 300, base component 1300 may include grooves 1312 in the keel 1350 where the base portion 1310 transitions into the keel 1350, with the grooves 1312 contoured to provide clearance for fixation members 400 that extend through the corresponding apertures 1320. In order to facilitate a later revision procedure, apertures 1320 may be utilized after the fixation members 1400 are removed. In other words, a cutting tool may be passed through the apertures 1320 on the anterior and posterior sides of the keel 1350 to ream away bone that has grown into the implant 1100, for example including into enhanced bone-ingrowth surfaces on the anterior and posterior sides of the keel 1350. Otherwise, the implantation and revision procedures for glenoid implant 1100 are substantially similar to those described above in connection with glenoid implant 100.

FIGS. 14-18 illustrate components of a glenoid implant 2100 according to another embodiment of the disclosure. It should be understood that glenoid implant 2100 has many similar or identical features to glenoid implant 100, and thus only the differences are described in connection with glenoid implant 2100. In other words, unless noted otherwise, the components of glenoid implant 2100 are similar or the same as those described for glenoid implant 100, including possible variations described in connection with glenoid implant 100.

Figure 14:
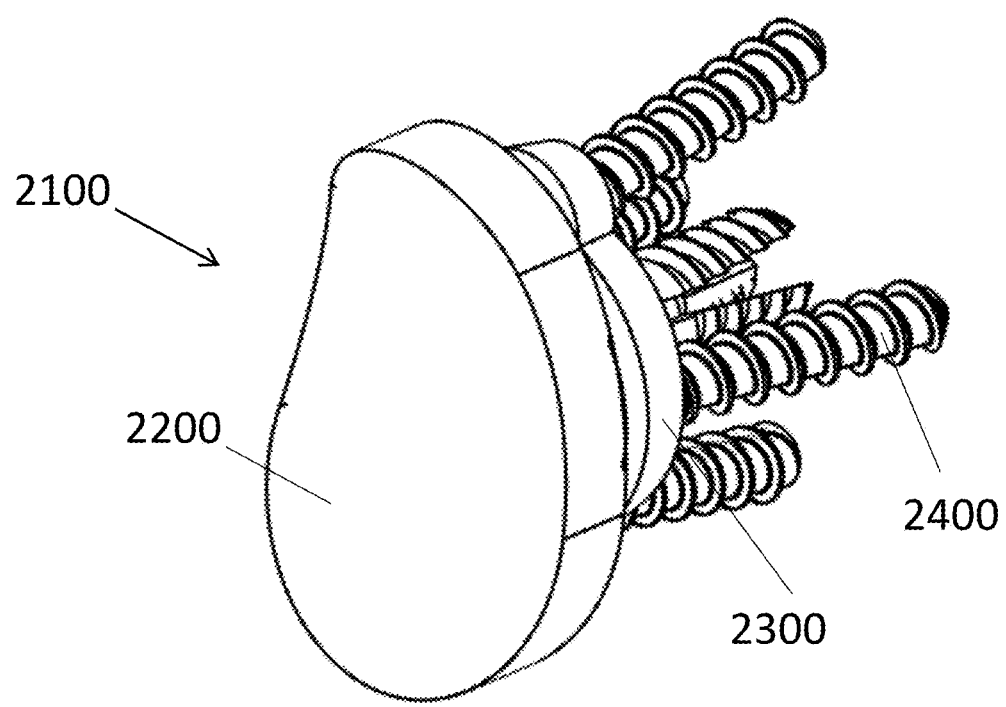
FIGS. 14-15 are perspective views of a prosthetic glenoid implant according to a further aspect of the disclosure.
Figure 15:
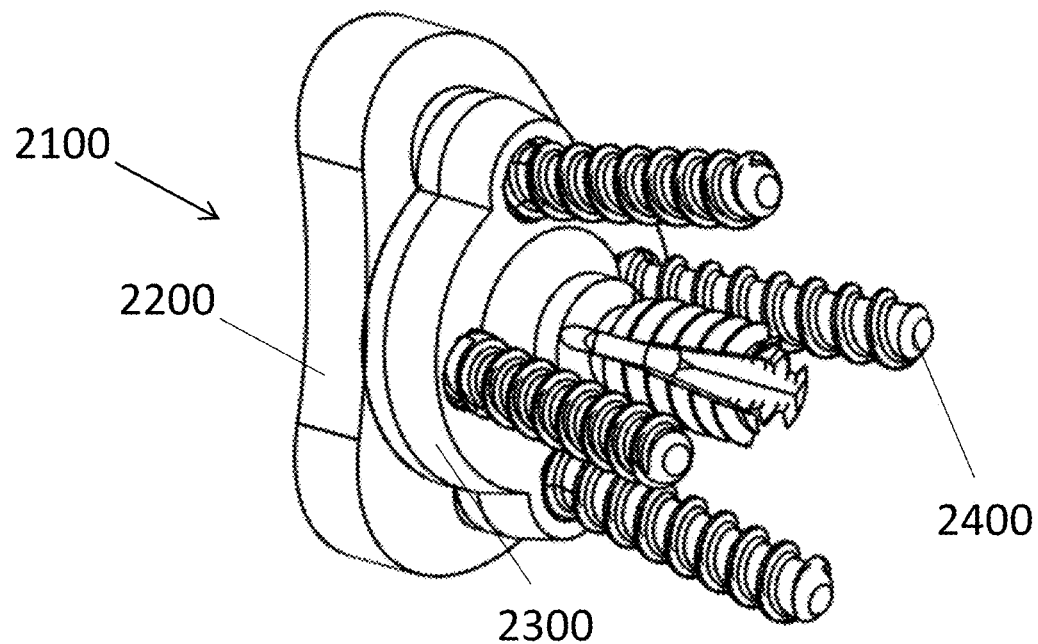

FIGS. 14-15 are perspective views of glenoid implant 2100. Similar to glenoid implant 100, implant 2100 includes a bearing component 2200, a base component 2300, and fixation members 2400. Bearing component 2200 may be similar or identical to bearing component 200, and thus is not described in greater detail herein.

Figure 16:
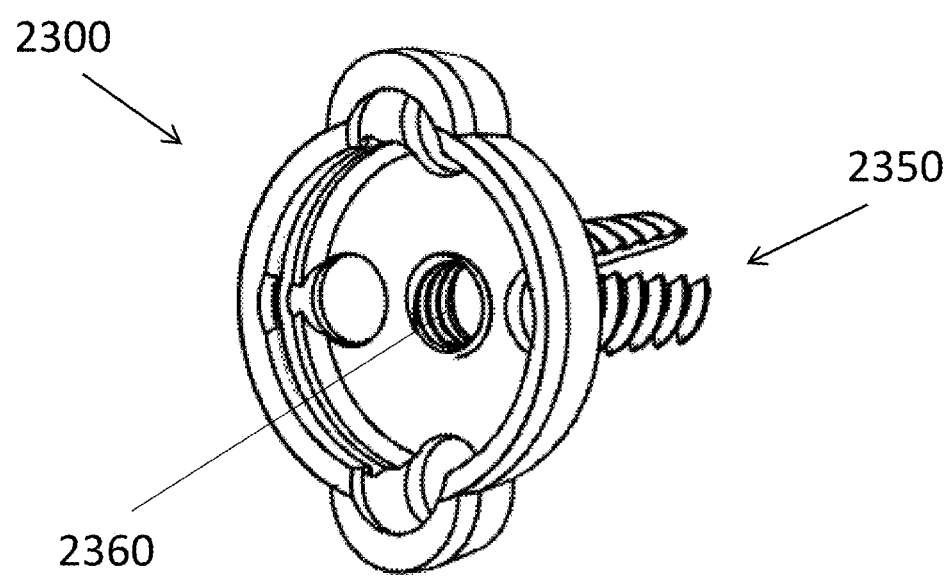
FIGS. 16-17 are perspective views of a base component of the glenoid implant of FIGS. 14-15.
Figure 17:
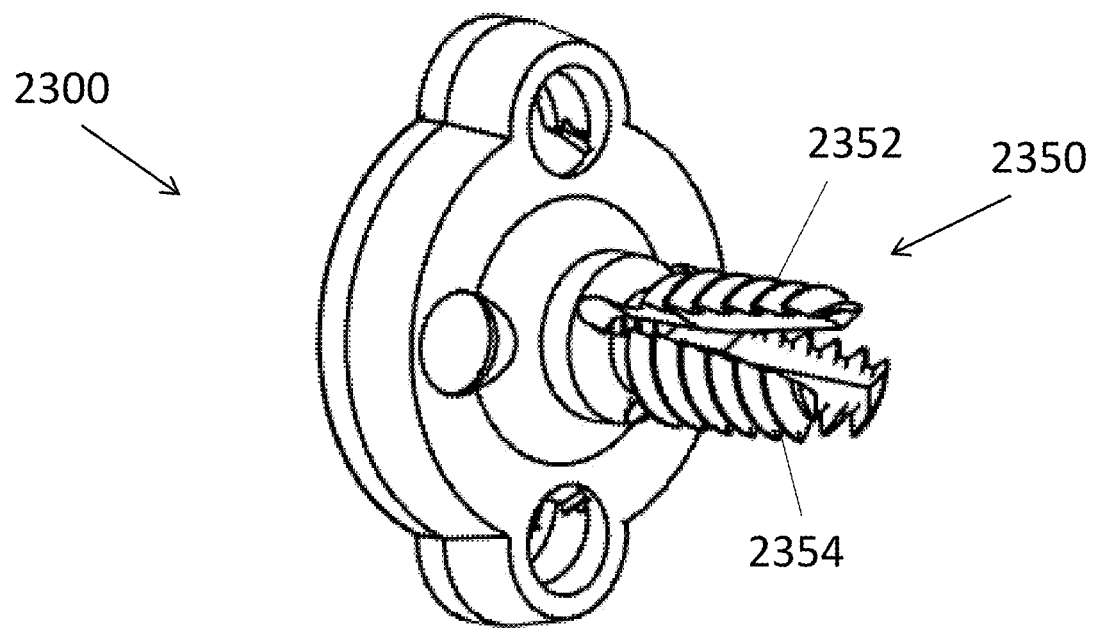

FIGS. 16-17 are perspective views of base component 2300, which may be substantially similar to base component 300, with certain exceptions described below. Most notably, base component 1300 includes a collet anchor 2350 instead of the type of keel 350 of base component 300. Collet anchor 2350 may extend medially from a point at substantially at the radial center of base component 2300. In the illustrated example, collet anchor 2350 includes a plurality of splaying members 2352 adapted to splay away from one another upon the application of force. In the particular illustrated embodiment, collet anchor 2350 includes three splaying members 2352 that each include frictional engagement features, for example ribs 2354. In FIGS. 16 and 17, collet anchor 2350 is illustrated in a splayed condition. It should be understood that, prior to implantation and prior to application of force, the collet anchor 2350 may be in a non-splayed condition. Preferably, collet anchor 2350 is formed from a metal or metal alloy, such as titanium.

Figure 18:
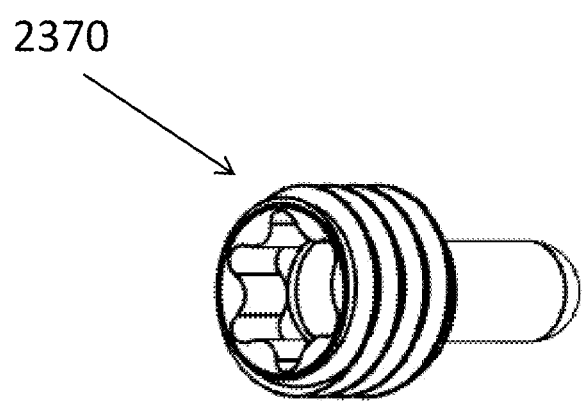
FIG. 18 is a perspective view of a collet screw for use with the base component of FIGS. 16-17.

Referring to FIG. 16, base component 2300 may include a central aperture 2360, preferably including threads, which opens to an interior surface of collet anchor 2350. Referring to FIG. 18, glenoid implant 2300 may include a collet screw 2370. Collet screw 2370 may include a threaded head portion a shaft portion. In use, the shaft portion of the collet screw 2370 may be passed through the central aperture 2360 and the collet screw 2370 may be advanced until the threaded head of the collet screw 2370 engages the corresponding threads in central aperture 2360. The collet screw 2370 may be advanced via rotation, for example via a screw driver. As the collet screw 2370 advances, the shaft of the collet screw advances and forces the splaying members 2352 of the collet anchor 2350 to splay radially outward away from each other.

In an exemplary method of implantation of glenoid implant 2100, after preparing the native glenoid, the base component 2300 of glenoid implant 2100 may first be inserted into the glenoid vault while the collet anchor 2350 is in the non-splayed condition. Then, fixation members 2400 may be inserted through the peripheral apertures and into the bone to secure the base component 2300 to the glenoid. Either before or after inserting the fixation members 2400, the collet screw 2370 may be rotated to cause the splaying members 2353 of the collet anchor 2350 to splay outwardly, to further enhance the fixation of the base component 2300 to the glenoid. With the base component 2300 fixed in place, the remainder of the glenoid implant may be assembled in substantially the same fashion as described above in connection with glenoid implant 100. Although either order is suitable, it may be preferable to place the fixation members 2400 prior to activating the collet anchor 2350 to limit the stresses on the collet anchor 2350 after the collet is deployed.

During a revision procedure, after the bearing component 2200 is removed from the base component 2300, the fixation members 2400 may be removed, and the collet screw 2370 removed to allow the collet anchor 2350 to un-splay, at which point the collet anchor 2350 may also be removed from the bone.

Figure 19:
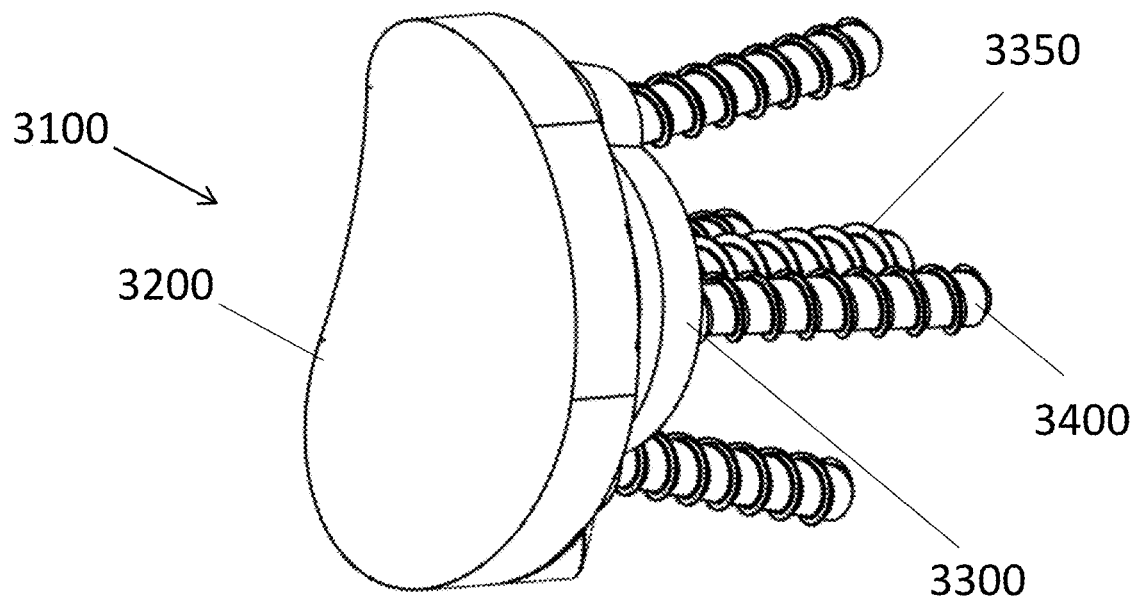
FIGS. 19-20 are perspective views of a prosthetic glenoid implant according to another aspect of the disclosure.
Figure 20:
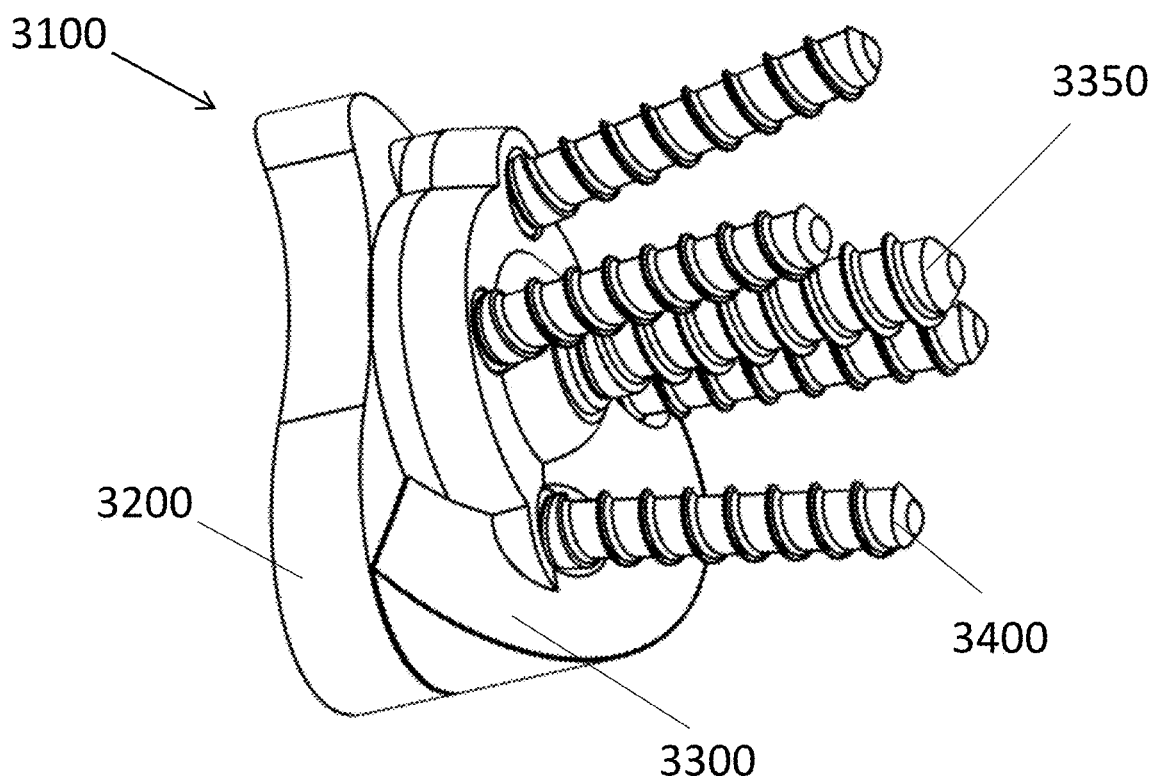

FIGS. 19-20 are perspective views of glenoid implant 3100. Similar to glenoid implant 100, implant 3100 includes a bearing component 3200, a base component 3300, and fixation members 3400. Bearing component 3200 may be similar or identical to bearing component 200, and thus is not described in greater detail herein.

Figure 21:
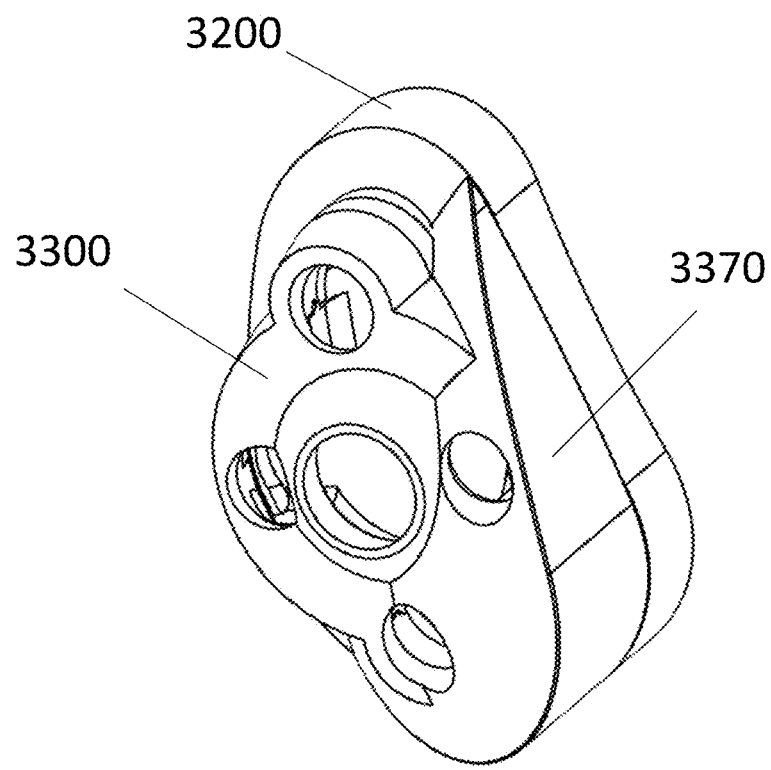
FIG. 21 is a perspective view of a bearing component and a base component of the implant of FIGS. 19-20.
Figure 22:
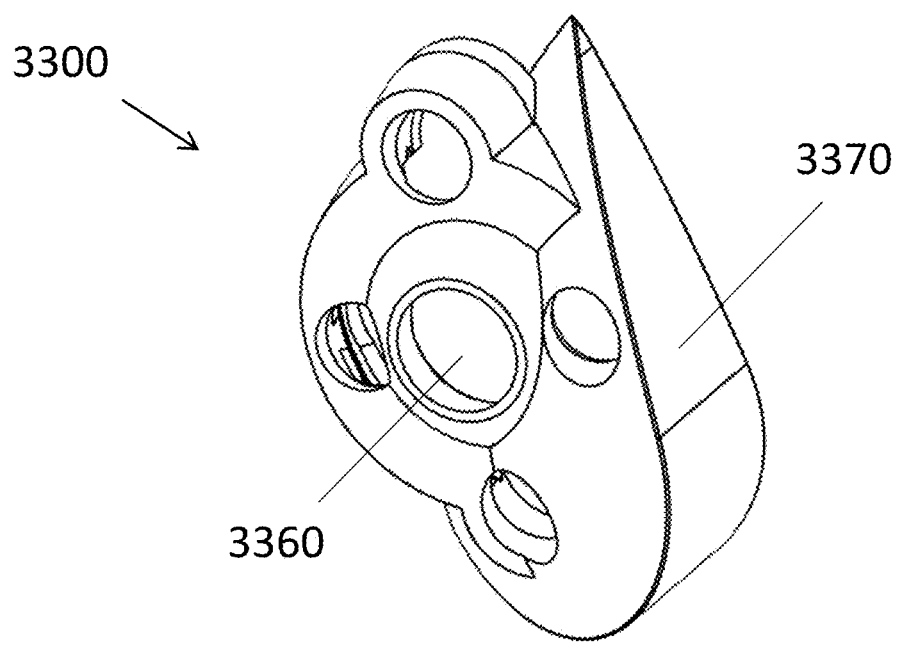
FIGS. 22-23 are perspective views of the base component of the implant of FIGS. 19-20.
Figure 23:
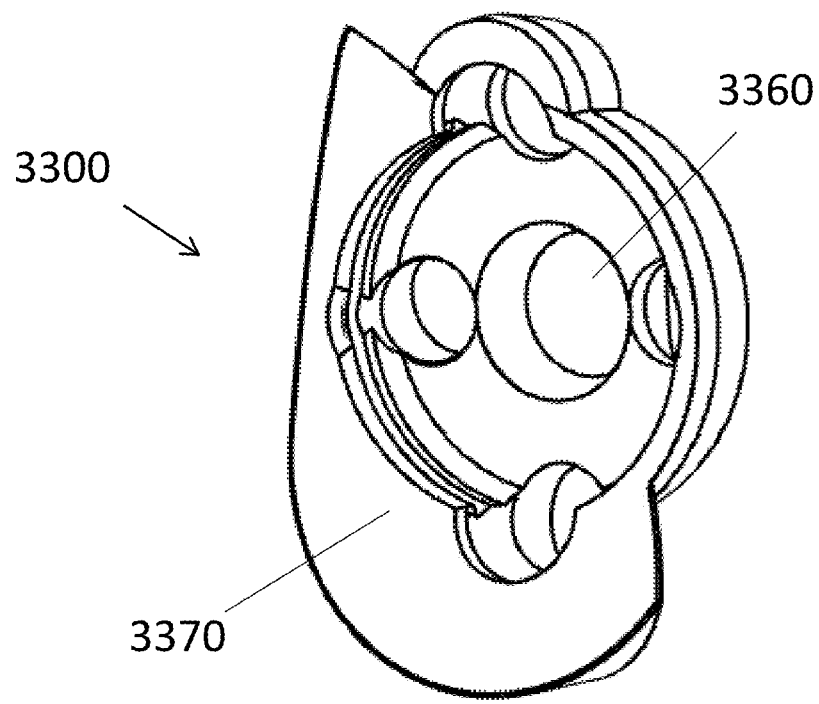

FIG. 21 is a perspective view of bearing component 3200 coupled to base component 3300, with fixation members 3400 and center anchor 3350 omitted for purposes of illustration. FIGS. 22 and 23 are perspective views of bearing component 3200 isolated from other components of the system. Base component 3300 may be substantially similar to base component 300, with certain exceptions described below. Most notably, base member 3300 includes an augment portion 3370, and includes a central aperture 3360 for receiving a central anchor 3350 instead of the keel 350 of base component 330.

Referring to FIGS. 21-23, base component 2300 includes a central aperture 3360 for receiving a center anchor 3350. Center anchor 3350, which is illustrated in FIGS. 19-20, may be a threaded screw similar to fixation members 3400. However, in some embodiments, center anchor 3350 may be larger (e.g. have a larger diameter) than the other fixation members 3400. Functionally, the center anchor 3350 may assist in securing the base component 3300 to the glenoid, with the remaining fixation members 3400 further helping in the initial securement of the implant 3100. Preferably, the center anchor 3350 may be locked into the base component 3300 to better assist in the overall long-term fixation of the implant 3100. As with the other fixation members 3400, center anchor 3450 is preferably formed of a biocompatible metal or metal alloy.

Still referring to FIGS. 21-23, base component 3300 may be mostly similar to base component 300, for example including the plurality of apertures for receiving the fixation members 3400, as well as recesses and/or rims to allow for the base component 3300 to couple to bearing component 3200, for example including via a snap-fit. In addition to central aperture 3360, the other main difference between base component 3300 and base component 300 is the inclusion of the augment portion 3700. Augment portion 3700 may be generally ramped and include a convex or partially-convex bone-contacting surface, at least a portion of which extends farther away from bearing component 3200 than other portions of base component 3300. Augment portion 3700 may be sized and shaped to be implanted on a concave neoglenoid portion of the glenoid that has experienced a partial wear pattern, such as that classified as B2 Walch type of glenoid wear. In the illustrated example, two of the apertures adapted to receive fixation members 3400 are positioned within the augment portion 3700 of the base component 3300, although more or fewer apertures may be positioned within the augment portion 3700 in other embodiments.

Further examples of augmented glenoid designs that may be suitable for use with glenoid implant 3100 are described in greater detail in U.S. Provisional Patent Application No. 62/873,266, titled "Augmented Glenoid Design," the contents of which are hereby incorporated by reference herein. Although one particular size of augmented portion 3700 is illustrated in connection with glenoid implant 3100, it should be understood that a single bearing component 3200 may be provided with a set of base components 3300 that differ in the size of the augmented portion 3700, so that a user, such as a surgeon, may use a base component 3300 having an augmented portion 3700 that best matches the specific glenoid wear pattern of the patient being treated.

During implantation, the neoglenoid and paleoglenoid surface of the glenoid may need to be reamed first and osteophytes removed to prepare the bone. Although the fixation members 3400 may be placed in any desired order, it may be preferable to place the fixation members 3400 in the neoglenoid bone first, for example to ensure the best fit to the strongest bone. However, any order may be suitable.

Although the invention herein has been described with reference to particular embodiments, it is to be understood that these embodiments are merely illustrative of the principles and applications of the present invention. It is therefore to be understood that numerous modifications may be made to the illustrative embodiments and that other arrangements may be devised without departing from the spirit and scope of the present invention as defined by the appended claims.

The invention claimed is:

1. A prosthetic glenoid implant for replacing a native glenoid, the prosthetic glenoid implant comprising:
   a bearing component having a first articulating surface adapted to articulate with a native or prosthetic humeral head, and a second surface opposite the first surface, the bearing component being formed of a polymer, the second surface including a first mating feature;
   a base component having a first surface and a bone-contacting surface, the first surface of the base component having a second mating feature adapted to engage the first mating feature in an assembled condition of the prosthetic glenoid implant, the bone-contacting surface adapted to contact the native glenoid, the base component being formed of metal and defining a plurality of apertures extending from the first surface of the base component to the bone-contacting surface of the base component, the base component including a keel extending away from the bone-contacting surface, the keel having a length in a length direction extending away from the bone-contacting surface, a height in a first direction transverse to the length direction, and a width in a second direction transverse the length direction and the first direction, the width being smaller than the length and the height; and
   a plurality of fixation members each having a head and a threaded shaft, the threaded shaft of each fixation member adapted to pass through a corresponding one of the plurality of apertures, the head of each fixation member adapted to be positioned within a recess defined between the base component and the bearing component in an assembled condition of the prosthetic glenoid implant,
   wherein the base component includes a base portion having a generally circular shape interrupted by a superior extension extending superiorly from the generally circular shape and an inferior extension extending inferiorly from the generally circular shape, the superior and inferior extensions each including an aperture, said apertures in the superior and inferior extensions forming superior and inferior apertures for superior and inferior fixation members to extend therethrough so that the superior fixation member is positioned superior to the keel and the inferior fixation member is positioned inferior to the keel.

2. The prosthetic glenoid implant of claim 1, wherein the first mating feature is a peripheral recess and the second mating feature is a peripheral rim adapted to be received within the peripheral recess.

3. The prosthetic glenoid implant of claim 1, wherein the first mating feature is a peripheral rim and the second mating feature is a peripheral recess, the peripheral rim being adapted to be received within the peripheral recess.

4. The prosthetic glenoid implant of claim 1, wherein the keel is generally trapezoidal.

5. The prosthetic glenoid implant of claim 1, wherein the keel includes a window defining a recess.

6. The prosthetic glenoid implant of claim 5, wherein the recess is generally trapezoidal.

7. The prosthetic glenoid implant of claim 5, wherein the recess includes an array of circular openings.

8. The prosthetic glenoid implant of claim 1, wherein the base component includes a first slot extending from the first surface of the base component to the bone-contacting surface of the base component, the first slot being positioned adjacent the keel on a first side of the keel.

9. The prosthetic glenoid implant of claim 8, wherein the base component includes a second slot extending from the first surface of the base component to the bone-contacting surface of the base component, the second slot being positioned adjacent the keel on a second side of the keel opposite the first side of the keel.

10. The prosthetic glenoid implant of claim 1, wherein the second surface of the bearing component includes a substantially circular extension member, the extension member having a plurality of recesses interrupting the circular extension member to define a plurality of individual extension members.

11. The prosthetic glenoid implant of claim 10, wherein each of the individual extension members includes an anti-rotation protrusion extending in a direction radially away from a center of the circular extension member.

12. The prosthetic glenoid implant of claim 11, wherein the first surface of the base component includes a substantially circular member interrupted by a plurality of notches, each anti-rotation protrusion adapted to be received within a corresponding one of the plurality of notches in an assembled condition of the prosthetic glenoid implant.

13. The prosthetic glenoid implant of claim 1, wherein the keel includes grooves where the superior and inferior extensions of the base portion transition into the keel, the grooves contoured to provide clearance for superior and inferior fixation members that extend through the superior and inferior apertures.

14. A prosthetic glenoid implant for replacing a native glenoid, the prosthetic glenoid implant comprising:
a bearing component having a first articulating surface adapted to articulate with a native or prosthetic humeral head, and a second surface opposite the first surface, the bearing component being formed of a polymer, the second surface including a first mating feature;
a base component having a first surface and a bone-contacting surface, the first surface of the base component having a second mating feature adapted to engage the first mating feature in an assembled condition of the prosthetic glenoid implant, the bone-contacting surface adapted to contact the native glenoid, the base component being formed of metal and defining a plurality of apertures extending from the first surface of the base component to the bone-contacting surface of the base component, the base component including a keel extending away from the bone-contacting surface, the keel having a length in a length direction extending away from the bone-contacting surface, and a width in a direction transverse the length direction, the width being smaller than the length; and
a plurality of fixation members each having a head and a threaded shaft, the threaded shaft of each fixation member adapted to pass through a corresponding one of the plurality of apertures, the head of each fixation member adapted to be positioned within a recess defined between the base component and the bearing component in an assembled condition of the prosthetic glenoid implant,
wherein the base component includes a base portion having a generally circular shape interrupted by a superior extension extending superiorly from the generally circular shape and an inferior extension extending inferiorly from the generally circular shape, the superior and inferior extensions each including an aperture, said apertures in the superior and inferior extensions forming superior and inferior apertures for superior and inferior fixation members to extend therethrough so that the superior fixation member is positioned superior to the keel and the inferior fixation member is positioned inferior to the keel, and
wherein the base component includes a first slot extending from the first surface of the base component to the bone-contacting surface of the base component, the first slot being positioned adjacent the keel on a first side of the keel.

15. A prosthetic glenoid implant for replacing a native glenoid, the prosthetic glenoid implant comprising:
a bearing component having a first articulating surface adapted to articulate with a native or prosthetic humeral head, and a second surface opposite the first surface, the bearing component being formed of a polymer, the second surface including a first mating feature;
a base component having a first surface and a bone-contacting surface, the first surface of the base component having a second mating feature adapted to engage the first mating feature in an assembled condition of the prosthetic glenoid implant, the bone-contacting surface adapted to contact the native glenoid, the base component being formed of metal and defining a plurality of apertures extending from the first surface of the base component to the bone-contacting surface of the base component, the base component including a keel extending away from the bone-contacting surface, the keel having a length in a length direction extending away from the bone-contacting surface, and a width in a direction transverse the length direction, the width being smaller than the length; and
a plurality of fixation members each having a head and a threaded shaft, the threaded shaft of each fixation member adapted to pass through a corresponding one of the plurality of apertures, the head of each fixation member adapted to be positioned within a recess defined between the base component and the bearing component in an assembled condition of the prosthetic glenoid implant,
wherein the base component includes a base portion having a generally circular shape interrupted by a superior extension extending superiorly from the generally circular shape and an inferior extension extending inferiorly from the generally circular shape, the superior and inferior extensions each including an aperture, said apertures in the superior and inferior extensions forming superior and inferior apertures for superior and inferior fixation members to extend therethrough so that the superior fixation member is positioned superior to the keel and the inferior fixation member is positioned inferior to the keel, and
wherein the first mating feature is a peripheral rim and the second mating feature is a peripheral recess, the peripheral rim being adapted to be received within the peripheral recess.

* * * * *